US010007020B2

(12) United States Patent
Li et al.

(10) Patent No.: US 10,007,020 B2
(45) Date of Patent: Jun. 26, 2018

(54) VEHICLE INSPECTION SYSTEM AND METHOD WITH VEHICLE REFERENCE IMAGE RETRIEVAL AND COMPARISON FUNCTION (71) Applicant: Nuctech Company Limited, Haidian District, Beijing (CN)

(72) Inventors: Jianmin Li, Beijing (CN); Ying Li, Beijing (CN); Yulan Li, Beijing (CN); Jianping Gu, Beijing (CN); Yuanjing Li, Beijing (CN); Zhiqiang Chen, Beijing (CN)

(73) Assignee: Nuctech Company Limited, Haidian District, Beijing (CN)

( * ) Notice: Subject to any disclaimer, the term of this patent is extended or adjusted under 35 U.S.C. 154(b) by 174 days.

(21) Appl. No.: 14/970,679

(22) Filed: Dec. 16, 2015

(65) Prior Publication Data
US 2016/0178790 A1    Jun. 23, 2016

(30) Foreign Application Priority Data
Dec. 17, 2014 (CN) .......................... 2014 1 0787783

(51) Int. Cl.
*G06K 9/00*    (2006.01)
*G01V 5/00*    (2006.01)
(Continued)

(52) U.S. Cl.
CPC .......... *G01V 5/0016* (2013.01); *G01N 23/04* (2013.01); *G01V 5/0008* (2013.01); *G06K 9/00624* (2013.01); *G06K 9/52* (2013.01); *G06K 9/6215* (2013.01); *G06T 7/001* (2013.01); *G06T 7/60* (2013.01); *G06T 7/74* (2017.01);
(Continued)

(58) Field of Classification Search
CPC ...... G01N 23/00; G01N 23/04; G01V 5/0008; G01V 5/0016; G06K 9/52; G06K 9/6215; G06K 2209/09; G06K 2209/23; G06K 9/00624; G06T 2207/10116; G06T 2207/30268; G06T 7/60;
(Continued)

(56) References Cited

U.S. PATENT DOCUMENTS

| 8,586,955 | B2* | 11/2013 | Tay ........................... G21F 3/00 250/515.1 |
| 2007/0009136 | A1* | 1/2007 | Pawlenko ............ G06K 9/3241 382/104 |
| 2008/0136625 | A1* | 6/2008 | Chew ................... G01V 5/0008 340/540 |

* cited by examiner

Primary Examiner — Tom Y Lu
(74) Attorney, Agent, or Firm — Merchant & Gould P.C.

(57) ABSTRACT

A vehicle inspection method is disclosed, comprising steps of: implementing a ray scanning inspection on an inspected vehicle, so as to obtain a ray scanning inspection image of the inspected vehicle; extracting vehicle characteristic information; comparing the vehicle characteristic information of the inspected vehicle to vehicle reference characteristics stored in a database, selecting a closest vehicle reference characteristic which is closest to the vehicle characteristic information, and finding out a closest ray transmission reference image on the basis of a corresponding relationship between the vehicle reference characteristics and ray transmission reference images stored in the storage unit; determining a first distinguishing area of the ray scanning inspection image from the closest ray transmission reference image by comparing the ray scanning inspection image of the inspected vehicle to the closest ray transmission reference image. A vehicle inspection system is also disclosed.

17 Claims, 5 Drawing Sheets (51) Int. Cl.
  *G01N 23/04* (2018.01)
  *G06K 9/52* (2006.01)
  *G06K 9/62* (2006.01)
  *G06T 7/60* (2017.01)
  *G06T 7/00* (2017.01)
  *G06T 7/73* (2017.01)
(52) U.S. Cl.
  CPC ... *G01N 2223/639* (2013.01); *G06K 2209/09* (2013.01); *G06K 2209/23* (2013.01); *G06T 2207/10116* (2013.01); *G06T 2207/30112* (2013.01); *G06T 2207/30248* (2013.01); *G06T 2207/30268* (2013.01)
(58) Field of Classification Search
  CPC . G06T 2207/30112; G06T 2207/30248; G06T 7/001; G06T 7/0044; G06T 7/74
  See application file for complete search history.

VEHICLE INSPECTION SYSTEM AND METHOD WITH VEHICLE REFERENCE IMAGE RETRIEVAL AND COMPARISON FUNCTION

CROSS-REFERENCE TO RELATED APPLICATION

This application claims the benefit of Chinese Patent Application No. 201410787783.2 filed on Dec. 17, 2014 in the State Intellectual Property Office of China, the whole disclosure of which is incorporated herein by reference.

BACKGROUND OF THE INVENTION

Field of the Invention

The present disclosure generally relates to a field of radiation inspection, and specifically relates to a vehicle inspection method and system.

Description of the Related Art

X-ray radiation imaging technique is an important means to implement a security inspection on various vehicles. After a vehicle is imaged by an X-ray radiation imaging system, an inspector determines whether there are contraband items in the inspected vehicle by viewing and analyzing an X-ray scanned image, so as to achieve the security inspection.

In an actual security inspection case, false inspections frequently occur if the vehicle image scanned by X-ray is viewed only by naked eyes of the inspector to find relatively smaller entrained or contraband items hidden in the vehicle. It presents high dependence on experience of the inspector, and imposes high labor intensity to the inspector. Therefore, it is necessary to develop an automatic vehicle inspection technique to find the entrained or contraband items hidden in the vehicle. However, since there are a large number of vehicle types in reality and a structure of the vehicle itself makes highly adversely affection on an automatic marker of the image, it is desired to distinguish the structure of the vehicle itself from loaded items in the image.

SUMMARY OF THE INVENTION

In view of one or more problems in the prior art, a vehicle inspection method and system are provided.

According to one embodiment of the present invention, there is provided a vehicle inspection method, comprising steps of: implementing a ray scanning inspection on an inspected vehicle, so as to obtain a ray scanning inspection image of the inspected vehicle; extracting vehicle characteristic information; comparing the vehicle characteristic information of the inspected vehicle to vehicle reference characteristics stored in a storage unit, selecting a vehicle reference characteristic which is closest to the vehicle characteristic information, and finding out a closest ray transmission reference image on the basis of a corresponding relationship between the vehicle reference characteristics and ray transmission reference images stored in the storage unit; determining a first distinguishing area of the ray scanning inspection image from the closest ray transmission reference image by comparing the ray scanning inspection image of the inspected vehicle to the closest ray transmission reference image.

In one embodiment, the vehicle characteristic information is extracted from the ray scanning inspection image of the inspected vehicle. Further, the vehicle characteristic information is chosen from at least one of the following characteristics: a length, a width, or a height of the vehicle; a relative position of an interior part, an external part, an interior marker or an external marker of the vehicle; contents of the interior marker or the external marker of the vehicle.

In one embodiment, the vehicle characteristic information is extracted from a vehicle picture captured by an optical method using a wave, the wavelength of which is greater than an X-ray. Alternatively, the vehicle characteristic information is extracted by a sensor. Further, the vehicle characteristic information is chosen from at least one of the following characteristics: a length, a width, or a height of the vehicle; a relative position of an external part or an external marker of the vehicle; contents of the external marker of the vehicle.

In one embodiment, the method further comprises steps of: highlighting the first distinguishing area for a user in the ray scanning inspection image; and/or identifying a preset contraband item in the first distinguishing area.

In one embodiment, the step of "finding out a closest ray transmission reference image" comprises steps of: firstly selecting a plurality of related ray transmission reference images after comparing the vehicle characteristic information of the inspected vehicle to the vehicle reference characteristics stored in a storage unit, and then selecting the closest ray transmission reference image from the plurality of closer ray transmission reference images. Further, selecting the closest ray transmission reference image from the plurality of closer ray transmission reference images is performed by a manual and/or machine algorithm.

In one embodiment, a history inspection database in the storage unit is automatically updated according to the ray scanning inspection image obtained during each scanning.

In one embodiment, a vehicle type image library is stored in the storage unit; and the method further comprises steps of: selecting a corresponding vehicle type image from the vehicle type image library based on the vehicle characteristic information; and determining a second distinguishing area of the ray scanning inspection image from the selected vehicle type image by comparing the ray scanning inspection image of the inspected vehicle to the selected vehicle type image.

According to another embodiment of the present invention, there is provided a vehicle inspection system, comprising:

a ray scanning unit comprising a radiation source and a detector, which is configured for scanning an inspected vehicle so as to obtain a ray scanning inspection image;

an image processing unit configured to extract vehicle characteristic information from the ray scanning inspection image;

a storage unit configured to store ray transmission reference images and vehicle reference characteristics which are in correspondence with each other;

a comparison processing unit configured to compare the extracted vehicle characteristic information to the stored vehicle reference characteristics so as to find out a closest ray transmission reference image, and configured to compare the ray scanning inspection image of the inspected vehicle to the closest ray transmission reference image so as to determine a first distinguishing area of the ray scanning inspection image from the closest ray transmission reference image.

According to a further another embodiment of the present invention, there is provided a vehicle inspection system, comprising:

a ray scanning unit comprising a radiation source and a detector, which is configured for scanning an inspected vehicle so as to obtain a ray scanning inspection image;

a camera unit configured to capture a vehicle picture;

an image processing unit configured to extract vehicle characteristic information from the vehicle picture;

a storage unit configured to store ray transmission reference images and vehicle reference characteristics which are in correspondence with each other;

a comparison processing unit configured to compare the extracted vehicle characteristic information to the stored vehicle reference characteristics so as to find out a closest ray transmission reference image, and configured to compare the ray scanning inspection image of the inspected vehicle to the closest ray transmission reference image so as to determine a first distinguishing area of the ray scanning inspection image from the closest ray transmission reference image.

According to a yet another embodiment of the present invention, there is provided a vehicle inspection system, comprising:

a ray scanning unit comprising a radiation source and a detector, which is configured for scanning an inspected vehicle so as to obtain a ray scanning inspection image;

a sensor unit configured to extract vehicle characteristic information;

a storage unit configured to store ray transmission reference images and vehicle reference characteristics which are in correspondence with each other;

a comparison processing unit configured to compare the extracted vehicle characteristic information to the stored vehicle reference characteristics so as to find out a closest ray transmission reference image, and configured to compare the ray scanning inspection image of the inspected vehicle to the closest ray transmission reference image so as to determine a first distinguishing area of the ray scanning inspection image from the closest ray transmission reference image.

In one embodiment, the vehicle inspection system further comprises: a display unit configured to highlight the first distinguishing area for a user in the ray scanning inspection image.

In one embodiment, the storage unit comprises a vehicle type database module and a history inspection database module.

BRIEF DESCRIPTION OF THE DRAWINGS

To provide a better understanding, the aforementioned and other embodiments of the present invention will be further described in detail with reference to the accompanying drawings, in which.

DETAILED DESCRIPTION OF PREFERRED EMBODIMENTS OF THE IVENTION

The specific embodiments of the present disclosure will be described in detail below. It should be noted that the embodiments herein are used for illustration only, without limiting the present disclosure. In the description below, a number of specific details are explained to provide better understanding of the present disclosure. However, it is apparent to those skilled in the art that the present disclosure can be implemented without these specific details. In other embodiments, well known structures, materials or methods are not described specifically so as not to obscure the present disclosure.

Throughout the specification, the reference to "one embodiment," "an embodiment," "one example" or "an example" means that the specific features, structures or properties described in conjunction with the embodiment or example are included in at least one embodiment of the present disclosure. Therefore, the phrases "in one embodiment," "in an embodiment," "in one example" or "in an example" presented in various positions throughout the specification may not necessarily refer to the same embodiment or example. Furthermore, specific features, structures or properties may be combined into one or more embodiments or examples in any appropriate combination and/or sub-combination. Moreover, it should be understood for those skilled in the art that the term "and/or" used herein means any and all combinations of one or more listed items.

Figure 1A:
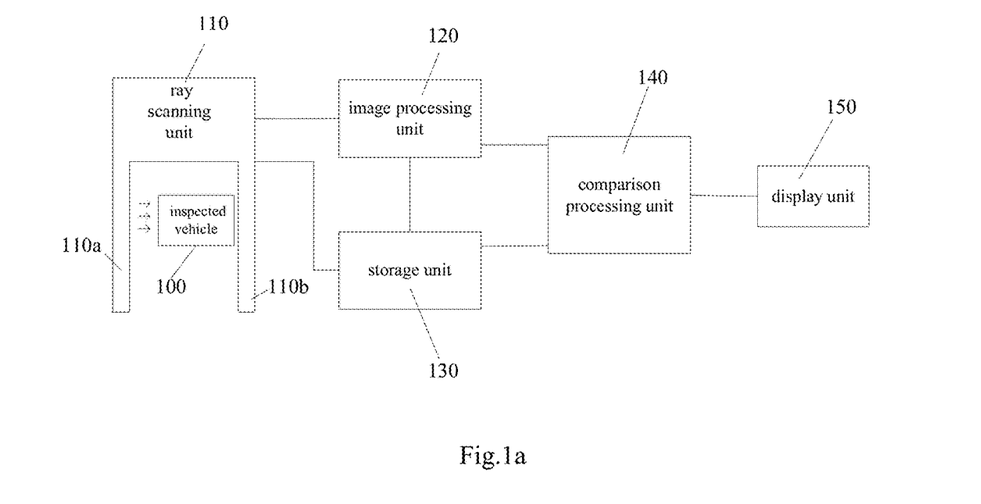
FIG. 1a is a structural schematic view of a vehicle inspection system according to an embodiment of the present invention.

FIG. 1 a is a structural schematic view of a vehicle inspection system according to an exemplary embodiment of the present invention. As shown in FIG. 1a, the vehicle inspection system according to an exemplary embodiment of the present invention comprises:

a ray scanning unit 110 for obtaining a ray scanning inspection image of a vehicle 100 to be inspected; the ray herein may be one or more ray chosen from X-ray, gamma ray, and neutron ray, and ray transmission reference images in a storage unit 130 mentioned hereafter may accordingly be X-ray reference images, gamma ray reference images, or neutron ray reference images;

an image processing unit 120 configured to extract vehicle characteristic information from the ray scanning inspection image which is an image obtained by scanning the inspected vehicle by the ray scanning unit 110 (if an accelerator is used as a radiation source, the ray scanning inspection image is an X-ray image);

a storage unit 130 configured to store ray transmission reference images and vehicle reference characteristics which are in correspondence with each other; and a comparison processing unit 140 configured to compare the extracted vehicle characteristic information to the stored vehicle reference characteristics so as to find out a closest ray transmission reference image, and configured to compare the ray scanning inspection image of the inspected vehicle to the closest ray transmission reference image so as to determine a first distinguishing area of the ray scanning inspection image from the closest ray transmission reference image.

Specifically, in the exemplary embodiment shown in FIG. 1a, the vehicle characteristic information may be chosen from at least one of the following characteristics: a length, a width or a height of the vehicle; a relative position of an interior part, an external part, an interior marker or an external marker of the vehicle; contents of the interior marker or the external marker of the vehicle.

Figure 1B:
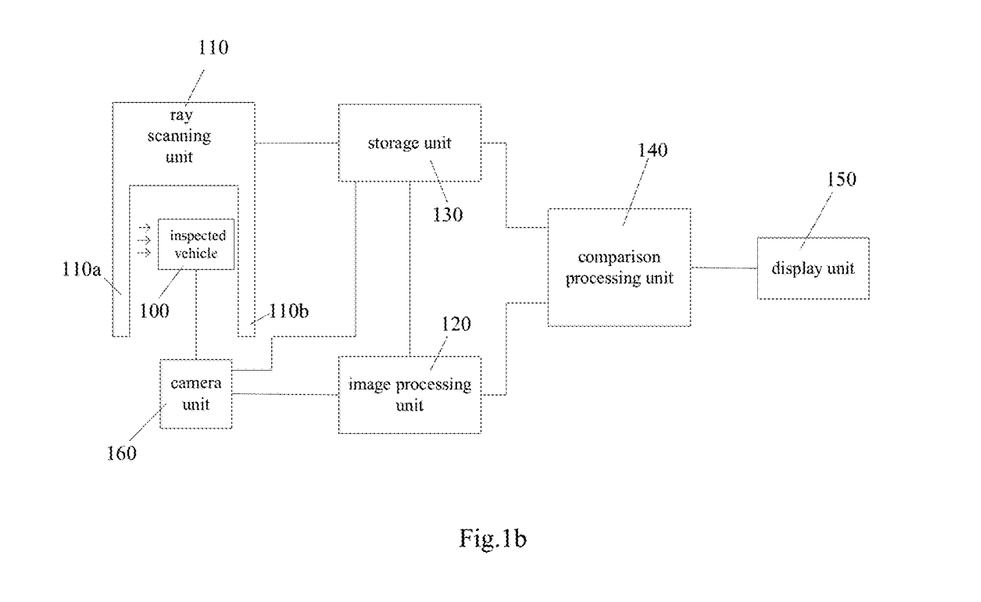
FIG. 1b is a structural schematic view of a vehicle inspection system according to another embodiment of the present invention.
Figure 1C:
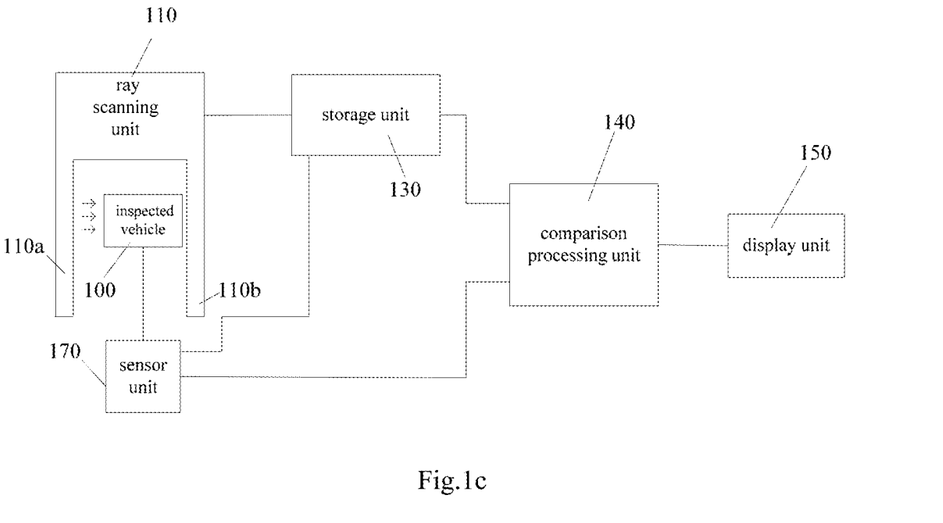
FIG. 1c is a structural schematic view of a vehicle inspection system according to a further embodiment of the present invention.

In the exemplary embodiment shown in FIG. 1a, the ray scanning inspection image is used to extract the vehicle characteristic information. Alternatively, as shown in FIG. 1b, a special camera may be used to capture a vehicle picture, the vehicle characteristic information is then extracted from the vehicle picture. In the latter case, the vehicle inspection system according to another exemplary embodiment of the present invention comprises:

a ray scanning unit 110 comprising a radiation source 110a and a detector 110b, which is configured for scanning an inspected vehicle so as to obtain a ray scanning inspection image;

a camera unit 160 for capturing a vehicle picture which may be captured by an optical method using a wave, the wavelength of which is greater than an X-ray, for example, using infrared, laser scanner, line-scan digital camera or visible light, etc.;

an image processing unit 120 configured to extract vehicle characteristic information from the vehicle picture;

a storage unit 130 configured to store ray transmission reference images and vehicle reference characteristics which are in correspondence with each other;

a comparison processing unit 140 configured to compare the extracted vehicle characteristic information to the stored vehicle reference characteristics so as to find out a closest ray transmission reference image, and configured to compare the ray scanning inspection image of the inspected vehicle to the closest ray transmission reference image so as to determine a first distinguishing area of the ray scanning inspection image from the closest ray transmission reference image. In the exemplary embodiment shown in FIG. 1c, a sensor is used to extract the vehicle characteristic information. In this case, the vehicle inspection system according to another exemplary embodiment of the present invention comprises:

a ray scanning unit 110 comprising a radiation source 110a and a detector 110b, which is configured for scanning an inspected vehicle so as to obtain a ray scanning inspection image;

a sensor unit 170 for extracting vehicle characteristic information;

a storage unit 130 configured to store ray transmission reference images and vehicle reference characteristics which are in correspondence with each other;

a comparison processing unit 140 configured to compare the extracted vehicle characteristic information to the stored vehicle reference characteristics so as to find out a closest ray transmission reference image, and configured to compare the ray scanning inspection image of the inspected vehicle to the closest ray transmission reference image so as to determine a first distinguishing area of the ray scanning inspection image from the closest ray transmission reference image.

In the embodiment shown in FIGS. 1b and 1c, the vehicle characteristic information may be chosen from at least one of the following characteristics: a length, a width or a height of the vehicle; a relative position of an external part or an external marker of the vehicle; contents of the external marker of the vehicle.

In the embodiment shown in FIG. 1c, the vehicle characteristic information, such as a length, a width or a height of the vehicle, or a length of axle shaft, a length of gap between a vehicle head and a carriage, etc., may be obtained by a plurality of position sensors or a combination of a position sensor with a velocity sensor. The position sensor may be a ground sensing coil, an electronic light curtain, an electronic switch or the like. The velocity sensor may be a speed measuring radar or the like. In particular, there are a large number of ways, for example, a length of the vehicle head, the length of gap between the vehicle head and the carriage, and a length of the carriage may be obtained by switching on/off a photoelectric switch in cooperation with the speed measuring radar.

Optionally, the vehicle inspection system further comprises a display unit 150 configured to highlight the first distinguishing area for a user in the ray scanning inspection image.

Figure 2A:
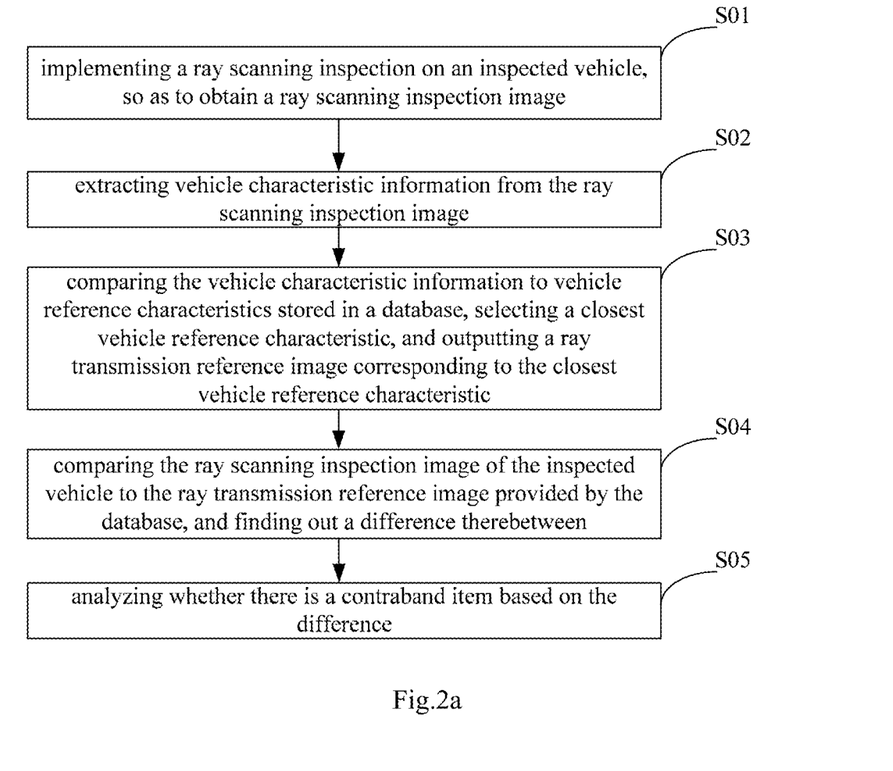
FIG. 2a is a flow chart schematically showing a vehicle inspection method according to an embodiment of the present invention.

FIG. 2a shows an exemplary embodiment of a vehicle inspection method according to the present invention, as shown in FIG. 2a, the method comprises steps of:

S01: implementing a ray scanning inspection on an inspected vehicle, so as to obtain a ray scanning inspection image;

S02: extracting vehicle characteristic information from the ray scanning inspection image;

S03: comparing the vehicle characteristic information to vehicle reference characteristics stored in a storage unit or a database, selecting a vehicle reference characteristic which is closest to the vehicle characteristic information, and outputting a closest ray transmission reference image which corresponds to the closest vehicle reference characteristic;

S04: comparing the ray scanning inspection image of the inspected vehicle to the ray transmission reference image provided by the storage unit or the database, and finding out a difference therebetween;

S05: analyzing whether there is a contraband item based on the difference.

Figure 2B:
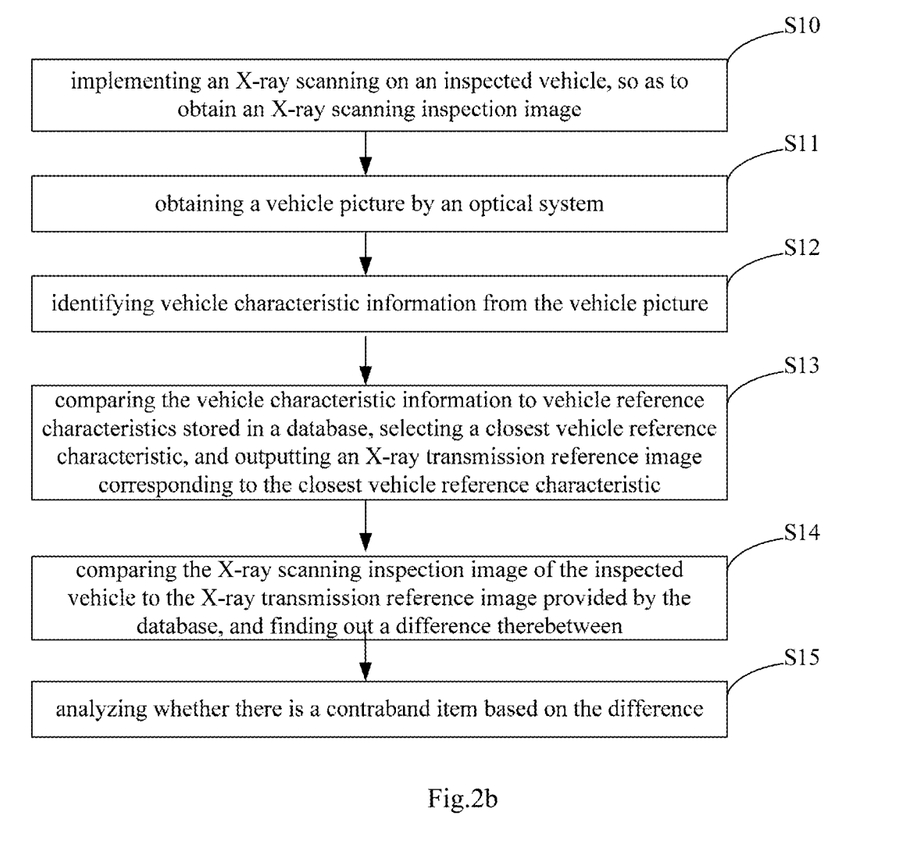
FIG. 2b is a flow chart schematically showing a vehicle inspection method according to another embodiment of the present invention.

FIG. 2b shows another exemplary embodiment of a vehicle inspection method according to the present invention, as shown in FIG. 2b, the method comprises steps of:

S10: implementing an X-ray scanning on an inspected vehicle, so as to obtain an X-ray scanning inspection image;

S11: obtaining a vehicle picture by an optical system;

S12: identifying vehicle characteristic information from the vehicle picture;

S13: comparing the vehicle characteristic information to vehicle reference characteristics stored in a storage unit or a database, selecting a vehicle reference characteristic which is closest to the vehicle characteristic information, and outputting an X-ray transmission reference image which corresponds to the closest vehicle reference characteristic;

S14: comparing the X-ray scanning inspection image of the inspected vehicle to the X-ray transmission reference image provided by the storage unit or the database, and finding out a difference therebetween;

S15: analyzing whether there is a contraband item based on the difference.

In summary, the present invention provides a vehicle inspection method, comprising steps of:

implementing a ray scanning inspection on an inspected vehicle, so as to obtain a ray scanning inspection image of the inspected vehicle;

extracting vehicle characteristic information;

comparing the vehicle characteristic information of the inspected vehicle to vehicle reference characteristics stored in a storage unit, selecting a vehicle reference characteristic which is closest to the vehicle characteristic information, and finding out a closest ray transmission reference image on the basis of a corresponding relationship between the vehicle reference characteristics and ray transmission reference images stored in the storage unit or the database;

determining a first distinguishing area of the ray scanning inspection image from the closest ray transmission reference image by comparing the ray scanning inspection image of the inspected vehicle to the closest ray transmission reference image.

Optionally, in the method described above, the vehicle characteristic information is chosen from at least one of the following characteristics: a length, a width or a height of the vehicle; a relative position of an interior part, an external part, an interior marker or an external marker of the vehicle; contents of the interior marker or the external marker of the vehicle.

Figure 3A:
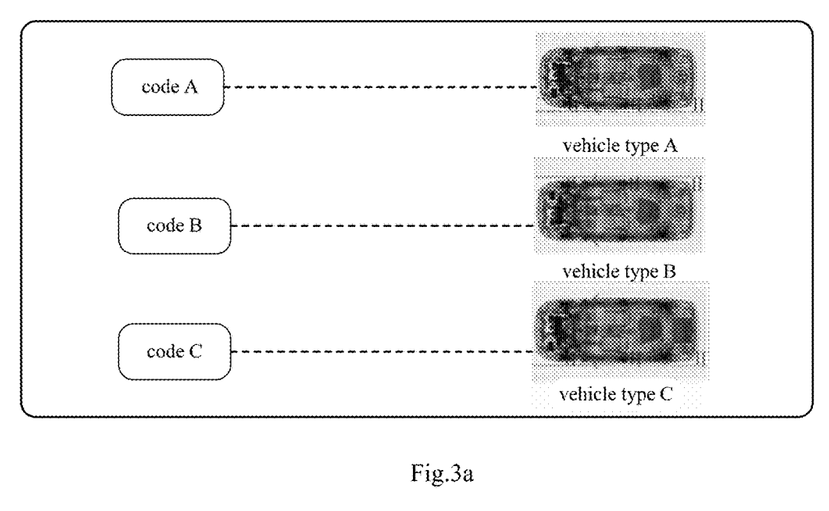
FIGS. 3a-3d show a corresponding relationship between vehicle reference characteristics and ray transmission reference images stored in the storage unit according to an embodiment of the present invention.

It should be noted that the "ray" herein may be one or more chosen from X-ray, gamma ray and neutron ray, and the ray transmission reference images in the storage unit or the database are accordingly X-ray transmission reference images, gamma ray transmission reference images, or neutron ray transmission reference images. For example, in an example shown in FIG. 3a, the ray transmission reference images are X-ray transmission reference images.

In an optional embodiment, the vehicle characteristic information is extracted from the ray scanning inspection image of the inspected vehicle. For example, as shown in FIG. 3c, the vehicle image of the inspected vehicle is just the ray scanning inspection image, by comparing it with close ray transmission reference images (vehicle Type A, vehicle type B, vehicle type C) stored in the storage unit or the database, an image of a vehicle type A is determined as the closest ray transmission reference image. Although an X-ray is used to obtain the vehicle image in the example shown in FIG. 3c, the vehicle image may also be obtained by an optical method using a wave, the wavelength of which is greater than an X-ray. In other words, in an optional embodiment, the vehicle characteristic information may be extracted from a vehicle picture captured by an optical method using a wave, the wavelength of which is greater than an X-ray. Such optical method captures the vehicle image, for example by means of infrared, visible light or millimeter-wave imaging, etc., as shown in FIG. 2b. In that case, external characteristics of the vehicle, i.e., various external characteristic information of the vehicle obtained by various optical methods, are correspondingly used as the vehicle reference characteristics stored in the storage unit or the database. Thus, after an external picture of the inspected vehicle is obtained by the optical method, corresponding vehicle characteristic information (or a whole picture) is extracted from the picture through a manual or computer algorithm, or a combination of manual algorithm with a computer algorithm, then it is compared with the vehicle reference characteristics stored in the storage unit or the database, so as to select a ray transmission reference image corresponding to the vehicle reference characteristic. Optionally, in the above method, the vehicle characteristic information is chosen from at least one of the following characteristics: a length, a width or a height of the vehicle; a relative position of an external part or an external marker of the vehicle; contents of the external marker of the vehicle.

In an optional embodiment, the vehicle characteristic information may be extracted by a sensor. In the embodiment shown in FIG. 1c, the vehicle characteristic information, such as a length, a width or a height of the vehicle, or a length of axle shaft, a length of gap between a vehicle head and a carriage, etc., may be obtained by a plurality of position sensors or a combination of a position sensor with a velocity sensor. The position sensor may be a ground sensing coil, an electronic light curtain, an electronic switch or the like. The velocity sensor may be a speed measuring radar or the like. In particular, there are a large number of ways, for example, a length of the vehicle head, the length of gap between the vehicle head and the carriage, and a length of the carriage may be obtained by switching on/off a photoelectric switch in cooperation with the speed measuring radar. Then, the data stored in the storage unit may be searched to find out a vehicle reference characteristic which matches with the obtained information and then find out a ray transmission reference image corresponding to the vehicle type stored in the storage unit, thereafter, the ray scanning inspection image is compared with the ray transmission reference image. Optionally, in the above described method, the vehicle characteristic information is chosen from at least one of the following characteristics: a length, a width or a height of the vehicle; a relative position of an external part or an external marker of the vehicle; contents of the external marker of the vehicle.

Optionally, the method further comprises steps of: highlighting the first distinguishing area for a user in the ray scanning inspection image; and/or identifying a preset contraband item in the first distinguishing area. It should be noted that it is possible to analyze or identify the contraband item by a manual way, or an automatic identification using a computer algorithm, or both.

The vehicle characteristic information may include vehicle type characteristic information and detailed vehicle information. For example, the vehicle type characteristic information may be a length, a width or a height of the vehicle, or a position of a part or a marker of the vehicle. The detailed vehicle information may be contents of the marker of the vehicle. In particular, the parts include a vehicle lamp, a tire, a wheel base, a chassis, a steering wheel, a seat, a vehicle housing, a car boot, etc.; the marker may be a vehicle brand, a chassis and/or a RFID, and any other arrangements providing an marker function for the vehicle.

The vehicle type characteristic information, such as the length, width or height of the vehicle, or the position of the part, may be directly measured by the sensor (such as an ultrasonic sensor, a photoelectric switch, a CCD camera, etc.) as described above, or may be obtained by a vehicle type identification algorithm after obtaining the vehicle image (such as X-ray image, an infrared image or a picture captured in visible light), that is, the vehicle type identification algorithm is used to extract the vehicle type characteristic.

An actual vehicle image (such as a X-ray scanning inspection image and an optical picture including visible light image, infrared light image and X-ray back scattering image, millimeter-wave scattering image, etc.) itself may be regarded as a vehicle reference characteristic. Under such a situation, it is possible to directly correspond the actual vehicle image with the ray transmission reference image stored in the storage unit or the database through the vehicle type identification algorithm. The vehicle type identification algorithm may be to make a direct subtracting image comparison on the actual vehicle image and the ray transmission reference images stored in the storage unit or the database, and to directly find out the distinguishing area. Then, a corresponding ray transmission reference image is found out based on the size of the distinguishing area (for example, the proportion of the distinguishing area to the ray transmission reference image, if the proportion is lower than 10%, they are considered to be similar). Alternatively, firstly, the importance of the position of the ray transmission reference images is ranked (for example, a chassis, a wheelbase and a vehicle housing contour act as a first region; the size of a tire, the location of a vehicle lamp, and the length, width or height of the vehicle act as a second region; the location of a seat, the size of a steering wheel and a vehicle logo act as a third region, and so on). Secondly, it is determined whether the actual vehicle image corresponds to the ray transmission reference image stored in the storage unit or the database according to the position of the distinguishing area in the ray transmission reference image (for example, if the distinguishing area of the actual vehicle image is focused on a rearview mirror, and the other areas are identical to that of one ray transmission reference image stored in the storage unit or the database, as the rearview mirror belongs to the third region in the vehicle type identification algorithm, it can be determined by the vehicle type identification algorithm that the actual vehicle image and such ray transmission reference image are of the same vehicle type), as shown in FIG. 3c.

Figure 3B:
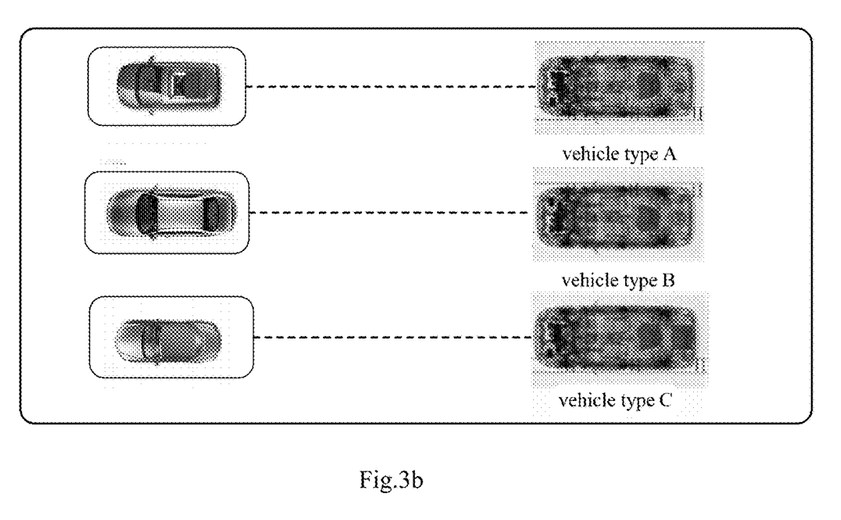
Figure 3C:
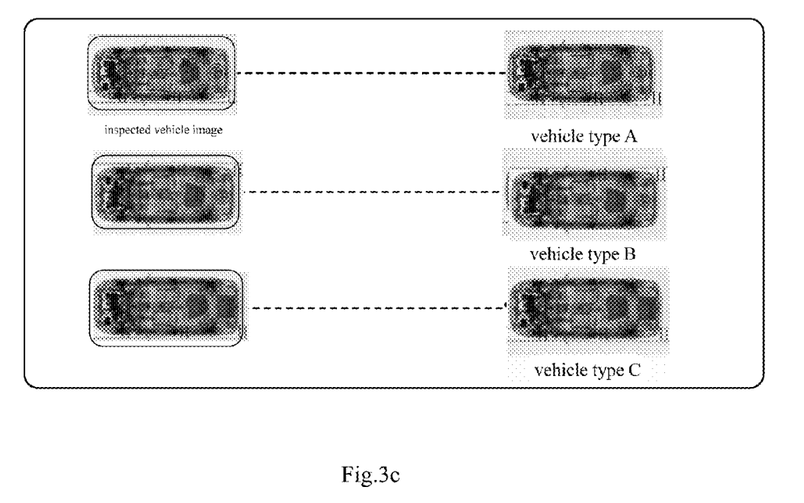
Figure 3D:
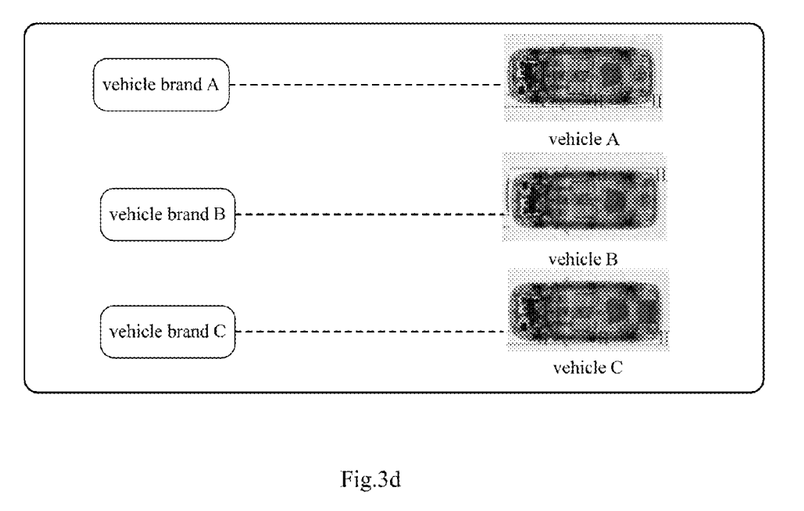

The content forms in the storage unit or the database is shown in FIGS. 3a-3d, which respectively correspond to a case in which the vehicle characteristic information refers to the length, width or height of the vehicle, or the position of the part or the marker of the vehicle (FIG. 3a), a case in which the vehicle characteristic information refers to the contents of the marker of the vehicle (FIG. 3d), a case in which the vehicle characteristic information refers to the image (FIG. 3b and FIG. 3c relate to the cases that the optical picture and the X-ray scanning inspection image of the vehicle correspond to the ray transmission reference image, respectively).

The storage unit or the database may comprise both a vehicle type database module and a history inspection database module. The vehicle type database module is used to store the vehicle reference characteristic for identifying the vehicle type, for example, the length, width or height of the vehicle, or the position of the part, or a vehicle type image, etc. The history inspection database module stores the updated vehicle image. A vehicle brand database module may be further included, which stores a corresponding relationship between the contents of the marker of the vehicle (such as a vehicle brand, a chassis, a RFID, or an ETC, etc.) and the ray transmission reference images. In the storage unit or the database, the various vehicle reference characteristics described above or a combination of a plurality of the vehicle reference characteristics are assigned a respective vehicle reference characteristic code, and the digitized vehicle reference characteristic codes are used for searching and comparing the ray transmission reference images in the storage unit or the database, as shown in FIGS. 3a-3d. In particular, in FIG. 3a, code A, code B, . . . , are the vehicle reference characteristic code, and in FIG. 3b, each of the optical pictures in left side corresponds to one vehicle reference characteristic code.

As for the case in which there are more than one vehicle reference characteristics which correspond to a ray transmission reference image, it is possible to assign a weight for each single different vehicle reference characteristic, and make a weighted combination of all the different vehicle reference characteristics, so as to match with the ray transmission reference image in the storage unit or the database. For example, a weight for the chassis is set as 30%, the wheel base is set as 20%, the body outer contour is set as 45%, and the rearview mirror is set as 5%; in the actual vehicle image, if the chassis and the body outer contour are identical to that of a ray transmission reference image numbered as 001, but the wheel base and the rearview mirror are not, then the matching degree of the actual vehicle image with the ray transmission reference image numbered as 001 is 30%+45%=75%, as a comparison, in the same actual vehicle image, if the wheel base and the chassis are identical to that of another ray transmission reference image numbered as 002, but the body outer contour and the rearview mirror are not, then the matching degree of the actual vehicle image with the ray transmission reference image numbered as 002 is 30%+20%=50%. After comparing the number 001 and the number 002, the vehicle type identification algorithm will select the ray transmission reference image numbered as 001 to be a corresponding image so as to implement a subsequent comparison with the scanning image.

In an optional embodiment, the step of "finding out a closest ray transmission reference image" comprises steps of: firstly selecting a plurality of closer ray transmission reference images after comparing the vehicle characteristic information of the inspected vehicle to the vehicle reference characteristics stored in a storage unit or a database, and then selecting the closest ray transmission reference image. Further specifically, the closest ray transmission reference image is selected from the plurality of related ray transmission reference images by a manual and/or machine algorithm.

In an optional embodiment, the storage unit or the database is automatically updated according to the vehicle image and/or the ray scanning inspection image obtained by each scanning.

A vehicle inspection method according to the vehicle type will be described below. It is possible to identify the inspected vehicle by means of a manual identification or by extracting a special characteristic from the obtained image. Specifically, the method comprises steps of: determining the vehicle type of the inspected vehicle (for example, based on the vehicle brand); selecting a vehicle type image corresponding to the vehicle type of the inspected vehicle from a vehicle type image library based on the vehicle type of the inspected vehicle; scanning the inspected vehicle to obtain a ray scanning inspection image of the inspected vehicle; and determining a distinguishing area of the ray scanning inspection image from the vehicle type image. According to the above method, the vehicle type image in the vehicle type image library is used to compare with the ray scanning inspection image of the inspected vehicle, so that the structure of the vehicle itself and the loaded items in the image may be distinguished from each other, thereby improving reliability and efficiency of the security inspection.

As another example, the vehicle inspection system according to the present disclosure has self-learning capability, i.e., the storage unit of the vehicle inspection system automatically updates the history inspection database in the storage unit according to the ray scanning inspection image obtained by each scanning, that is, during each inspection, the ray scanning inspection image of the inspected vehicle is stored as a history inspection image in the storage unit, so as to form a history inspection image library. Such storing may be in the form of replacing the original, corresponding ray scanning inspection image in the history inspection database, or in the form of adding the ray scanning inspection image newly obtained as a new image to the history inspection database. Thus, it is possible for the same vehicle type to add specific history inspection data of the vehicle gradually, enrich the contents of the database, and increase the number of the optional images. The history inspection database may be not only a history inspection database for storing the ray scanning inspection images, but also a history inspection database for storing the above-mentioned vehicle pictures.

In a case in which the storage unit has a history inspection database, the vehicle inspection method may comprise steps of: obtaining a unique identification number of the inspected vehicle (corresponding to the step of extracting the vehicle characteristic information); searching the history inspection database (corresponding to the ray transmission reference image) to find out at least one history inspection image which is related with the unique identification number; determining one of the at least one history inspection image as a template image (corresponding to the closest ray transmission reference image); and determining a distinguishing area of the ray scanning inspection image from the template image. Optionally, the template image is a history inspection image without any contraband item images; alternatively, it may be a history inspection image with a marked contraband item image.

The step of determining a distinguishing area of the ray scanning inspection image from the vehicle type image comprises steps of: matching the ray scanning inspection image with the vehicle type image; and calculating the difference between the matched ray scanning inspection image and vehicle type image.

The step of determining a distinguishing area of the ray scanning inspection image from the template image comprises steps of: matching the ray scanning inspection image with the template image; and calculating the difference between the matched ray scanning inspection image and template image.

While the present disclosure has been described with reference to several typical embodiments, it is apparent to those skilled in the art that the terms are used for illustration and explanation purpose and not for limitation. The present disclosure may be practiced in various forms without departing from the spirit or essence of the present disclosure. It should be understood that the embodiments are not limited to any of the foregoing details, and shall be interpreted broadly within the spirit and scope as defined by the following claims. Therefore, all of modifications and alternatives falling within the scope of the claims or equivalents thereof are to be encompassed by the claims as attached.

What is claimed is:

1. A vehicle inspection method, comprising steps of:
    implementing a ray scanning inspection on an inspected vehicle, so as to obtain a ray scanning inspection image of the inspected vehicle;
    extracting vehicle characteristic information;
    comparing the vehicle characteristic information of the inspected vehicle to vehicle reference characteristics stored in a storage, selecting a vehicle reference characteristic which is closest to the vehicle characteristic information, and finding out a closest ray transmission reference image on the basis of a corresponding relationship between the vehicle reference characteristics and ray transmission reference images stored in the storage;
    determining a first distinguishing area of the ray scanning inspection image from the closest ray transmission reference image by comparing the ray scanning inspection image of the inspected vehicle to the closest ray transmission reference image; and
    wherein the step of finding out the closest ray transmission reference image comprises steps of:
    firstly selecting a plurality of closer ray transmission reference images after comparing the vehicle characteristic information of the inspected vehicle to the vehicle reference characteristics stored in a storage, and then selecting the closest ray transmission reference image from the plurality of closer ray transmission reference images.

2. The vehicle inspection method according to claim 1, wherein the vehicle characteristic information is extracted from the ray scanning inspection image of the inspected vehicle.

3. The vehicle inspection method according to claim 1, wherein the vehicle characteristic information is extracted from a vehicle picture captured by an optical method using a wave which has a wavelength greater than X-ray.

4. The vehicle inspection method according to claim 1, wherein the vehicle characteristic information is obtained by a sensor.

5. The vehicle inspection method according to claim 1, further comprising steps of:
    highlighting the first distinguishing area for a user in the ray scanning inspection image; and/or
    identifying a preset contraband item in the first distinguishing area.

6. The vehicle inspection method according to claim 2, wherein the vehicle characteristic information is chosen from at least one of the following characteristics:
    a length, a width or a height of the vehicle;
    a relative position of an interior part, an external part, an interior marker or an external marker of the vehicle;
    contents of the interior marker or the external marker of the vehicle.

7. The vehicle inspection method according to claim 3, wherein the vehicle characteristic information is chosen from at least one of the following characteristics:
    a length, a width or a height of the vehicle;
    a relative position of an external part or an external marker of the vehicle;
    contents of the external marker of the vehicle.

8. The vehicle inspection method according to claim 1, wherein selecting the closest ray transmission reference image from the plurality of closer ray transmission reference images is performed by a manual and/or machine algorithm.

9. The vehicle inspection method according to claim 1, wherein a history inspection database in the storage is automatically updated according to the ray scanning inspection image obtained during each scanning.

10. The vehicle inspection method according to claim 1, wherein a vehicle type image library is stored in the storage; and
    the method further comprises steps of: selecting a corresponding vehicle type image from the vehicle type image library based on the vehicle characteristic information; and determining a second distinguishing area of the ray scanning inspection image from the selected vehicle type image by comparing the ray scanning inspection image of the inspected vehicle to the selected vehicle type image.

11. A vehicle inspection system, comprising:
    a ray scanning unit comprising a radiation source and a detector, which is configured for scanning an inspected vehicle so as to obtain a ray scanning inspection image;
    an image processor configured to extract vehicle characteristic information from the ray scanning inspection image;
    a storage;
    a processor configured to compare the extracted vehicle characteristic information to vehicle reference characteristics stored in the storage so as to find out a closest ray transmission reference image stored in the storage and in correspondence with the vehicle reference characteristics, and configured to compare the ray scanning inspection image of the inspected vehicle to the closest ray transmission reference image so as to determine a first distinguishing area of the ray scanning inspection image from the closest ray transmission reference image; and wherein the processor is configured to find out the closest ray transmission reference image by firstly selecting a plurality of closer ray transmission reference images after comparing the vehicle characteristic information of the inspected vehicle to the vehicle reference characteristics stored in a storage, and then selecting the closest ray transmission reference image from the plurality of closer ray transmission reference images.

12. A vehicle inspection system, comprising:
a ray scanning unit comprising a radiation source and a detector, which is configured for scanning an inspected vehicle so as to obtain a ray scanning inspection image;
a sensor unit configured to extract vehicle characteristic information;
a storage;
a processor configured to compare the extracted vehicle characteristic information to vehicle reference characteristics stored in the storage so as to find out a closest ray transmission reference image stored in the storage and in correspondence with the vehicle reference characteristics, and configured to compare the ray scanning inspection image of the inspected vehicle to the closest ray transmission reference image so as to determine a first distinguishing area of the ray scanning inspection image from the closest ray transmission reference image; and wherein the processor is configured to find out the closest ray transmission reference image by firstly selecting a plurality of closer ray transmission reference images after comparing the vehicle characteristic information of the inspected vehicle to the vehicle reference characteristics stored in a storage, and then selecting the closest ray transmission reference image from the plurality of closer ray transmission reference images.

13. The vehicle inspection system according to claim 11, further comprising a camera unit configured to capture a vehicle picture, and wherein the image processor is configured to extract vehicle characteristic information from the vehicle picture.

14. The vehicle inspection system according to claim 11, further comprising:
a display unit configured to highlight the first distinguishing area for a user in the ray scanning inspection image.

15. The vehicle inspection system according to claim 11, wherein the storage comprises a vehicle type database module and a history inspection database module.

16. The vehicle inspection system according to claim 12, further comprising:
a display unit configured to highlight the first distinguishing area for a user in the ray scanning inspection image.

17. The vehicle inspection system according to claim 12, wherein the storage comprises a vehicle type database module and a history inspection database module.

* * * * *